(12) United States Patent
Lips et al.

(10) Patent No.: US 9,918,653 B2
(45) Date of Patent: Mar. 20, 2018

(54) ELECTROPHYSIOLOGY CATHETER

(75) Inventors: Oliver Lips, Hamburg (DE); Bernd David, Huettblek (DE); Sascha Krueger, Hamburg (DE); Steffen Weiss, Hamburg (DE)

(73) Assignee: KONINKLIJKE PHILIPS ELECTRONICS N.V., Eindhoven (NL)

( * ) Notice: Subject to any disclaimer, the term of this patent is extended or adjusted under 35 U.S.C. 154(b) by 1449 days.

(21) Appl. No.: 13/142,432

(22) PCT Filed: Jan. 7, 2010

(86) PCT No.: PCT/IB2010/050052
§ 371 (c)(1),
(2), (4) Date: Jun. 28, 2011

(87) PCT Pub. No.: WO2010/082145
PCT Pub. Date: Jul. 22, 2010

(65) Prior Publication Data
US 2011/0275951 A1   Nov. 10, 2011

(30) Foreign Application Priority Data
Jan. 15, 2009  (EP) .................................. 09150590

(51) Int. Cl.
*A61B 5/053*   (2006.01)
*A61B 5/04*    (2006.01)
*A61B 5/042*   (2006.01)

(52) U.S. Cl.
CPC .............................. *A61B 5/0422* (2013.01)

(58) Field of Classification Search
USPC ................................................. 600/547, 592
See application file for complete search history.

(56) References Cited

U.S. PATENT DOCUMENTS

| | | | | |
|---|---|---|---|---|
| 5,341,807 A | * | 8/1994 | Nardella | 600/381 |
| 5,626,576 A | * | 5/1997 | Janssen | 606/41 |
| 5,643,255 A | * | 7/1997 | Organ | 606/41 |
| 5,788,692 A | * | 8/1998 | Campbell et al. | 606/33 |
| 5,820,568 A | | 10/1998 | Willis | |
| 5,836,874 A | * | 11/1998 | Swanson et al. | 600/374 |
| 6,064,905 A | * | 5/2000 | Webster et al. | 600/424 |

(Continued)

FOREIGN PATENT DOCUMENTS

| | | |
|---|---|---|
| EP | 1005838 A1 | 6/2000 |
| WO | 9712548 | 10/1996 |

(Continued)

*Primary Examiner* — Michael C Stout

(57) ABSTRACT

The invention relates to electrophysiology catheter systems and their use, such as in an MRI environment, and in particular to analysis of electric signals from such. An electrophysiology (EP) catheter with a plurality of electrically isolated electrode segments arranged in longitudinally spaced bands around the catheter is used to detect electric signals. A workstation receives the electrical signals which are then processed by a processing unit. Electric signals from electrode segments can be used to determine roll angle information of the catheter in relation to patient anatomy by determining signals from electrode segments in contact with tissue. Also, electric signals can be used to extract a reference signal that can be used to correct for gradient induced artifacts.

5 Claims, 5 Drawing Sheets

(56) References Cited

U.S. PATENT DOCUMENTS

| | | | |
|---|---|---|---|
| 6,569,160 B1* | 5/2003 | Goldin et al. | 606/41 |
| 7,047,068 B2* | 5/2006 | Haissaguerre | 600/547 |
| 7,983,793 B2* | 7/2011 | Toth et al. | 700/245 |
| 2002/0013613 A1* | 1/2002 | Haller et al. | 607/60 |
| 2002/0082665 A1* | 6/2002 | Haller et al. | 607/60 |
| 2003/0050557 A1 | 3/2003 | Susil et al. | |
| 2003/0097125 A1* | 5/2003 | Hall | 606/34 |
| 2003/0100895 A1* | 5/2003 | Simpson et al. | 606/41 |
| 2004/0092806 A1* | 5/2004 | Sagon et al. | 600/374 |
| 2004/0254622 A1* | 12/2004 | Shadduck | 607/99 |
| 2005/0033281 A1* | 2/2005 | Bowman et al. | 606/41 |
| 2005/0251156 A1* | 11/2005 | Toth et al. | 606/153 |
| 2006/0122673 A1* | 6/2006 | Callister et al. | 607/105 |
| 2006/0129142 A1* | 6/2006 | Reynolds | 606/21 |
| 2008/0009700 A1 | 1/2008 | Dumoulin et al. | |
| 2008/0125772 A1* | 5/2008 | Stone et al. | 606/41 |
| 2008/0140073 A1* | 6/2008 | Schwartz | 606/41 |
| 2008/0312521 A1* | 12/2008 | Solomon | 600/374 |
| 2008/0312713 A1* | 12/2008 | Wilfley et al. | 607/41 |
| 2010/0135553 A1* | 6/2010 | Joglekar | 382/128 |
| 2010/0152822 A1* | 6/2010 | Callister et al. | 607/105 |
| 2013/0096645 A1* | 4/2013 | Shadduck | 607/50 |

FOREIGN PATENT DOCUMENTS

| | | |
|---|---|---|
| WO | WO2008030789 | 3/2008 |
| WO | WO2008118992 | 10/2008 |
| WO | WO2008157399 | 12/2008 |

* cited by examiner

ELECTROPHYSIOLOGY CATHETER

FIELD OF THE INVENTION

The present invention relates to electrophysiology catheters, in particular to analysis of electric signals from such.

BACKGROUND OF THE INVENTION

Typical electrophysiology (EP) catheters have limited steering possibilities, and can usually only be bent in one direction transverse to the extent of the distal end of the catheter. Using this bending in combination with twisting or rolling the catheter to adjust a roll angle and thereby the direction of the bending, are the manoeuvres the operator uses to steer the catheter through the patient anatomy. It is therefore of importance for the operator to control the roll angle in relation to the patient anatomy, as this is needed to be able to bend the catheter tip in the right direction.

Steering catheters in patients is sometimes performed under guidance of a medical imaging modality, e.g. magnetic resonance imaging (MRI), but even this does not allow the operator to directly determine the catheter roll angle in relation to patient anatomy. Bending of the tip while monitoring it may give some indication, but this will only be conclusive for roll angles where the bending is transverse to the direction of imaging (i.e. in the image plane).

It is thereby a disadvantage that roll angle information is not directly available to the operator of EP catheters. Hence, an improved catheter system which could provide roll angle information would be advantageous.

Another problem when EP catheters are used in MRI environments is the presence of artefacts on the measured EP signal caused by the MR system. The switched gradient fields induce signal artefacts which contain similar frequencies as the physiological EP signal. Filtering these signals to reduce artefacts based on the gradient signal from the MRI apparatus is troublesome, as extracting and scaling an electrical signal proportional to the induced artefact is not simple. A data connection to the MR scanner has to be established and the retrieved gradient waveform has to be sampled and filtered in the same way as the EP signal. Furthermore, the relation of the gradient waveform to the actual artefact is often ambiguous.

It is thereby a disadvantage that gradient induced artefacts on signal measured by EP catheters in MRI environments cannot be efficiently filtered. Hence, an improved catheter system with improved electric signal filtering capabilities would be advantageous.

U.S. Pat. No. 5,788,692 discloses an EP catheter with ring electrodes that are segmented into separate electrode segments for the purpose of improving the spatial resolution of the acquired electrophysiology signals.

OBJECT OF THE INVENTION

It is a first object of the present invention to provide a system, a computer program and a method that solves the above mentioned problems of the prior art with determining roll angle information for EP catheters.

It is a second object of the present invention to provide a system, a computer program and a method that solves the above mentioned problems of the prior art with filtering gradient induced artefacts on EP signals measured with MR-EP catheters.

SUMMARY OF THE INVENTION

The above described first object is intended to be obtained, in a first aspect of the invention, by providing an electrophysiology catheter system comprising:
  an electrophysiology catheter with an elongated distal end portion having a centre axis and being bendable in at least one direction transverse to the centre axis, comprising:
  a plurality of electrically isolated electrode segments for detecting electrical signals and being arranged in two or more longitudinally spaced bands around said end portion;
  a plurality of electrode wires each coupled to an electrode segment and extending through the distal end portion to a proximal end portion of the electrophysiology catheter; and
  a workstation arranged to receive electrical signals detected by each electrode segment by means of the electrode wires coupled thereto and comprising a processing unit configured to identify electrode segments that are in contact with tissue from the received electrical signals by comparison of the electrical signal from each electrode segment with that from one or more other electrode segments or a predetermined threshold value and presenting the identified electrode segments to an operator with an indication of the identified electrode segments' position in relation to a bending direction or another marker of roll angle of the distal end portion.

In the following, a number of preferred and/or optional features and elements will be described in relation to various aspects and embodiments of the invention. Features or elements described in relation to one embodiment or aspect may be combined with or applied to the other embodiments or aspects where applicable.

The invention is particularly, but not exclusively, advantageous for obtaining information for an operator of which side of the EP catheter that touches the wall, which again enables the operator to steer the advancing catheter more precisely. This makes faster and safer advancement of EP catheters possible.

Therefore, in a preferred embodiment, the invention provides detailed information for the operator on the orientation and position of the EP catheter in that the workstation comprises a graphical user interface for presenting the positions of electrode segments identified to be in contact with tissue in relation to a bending direction or another marker of roll angle of the distal end portion.

The workstation preferably comprises circuitry with measurement section and sampling/multiplier section and being connected to each wire, and the processing unit preferably comprises a processor such as a CPU with access to data analysis algorithms implemented as computer programs or software that can be executed by the processor. The processing unit need not be one physical unit, but could be more units and more processors splitting the different tasks between them.

In the present context, tissue refers to connected tissue such as vessel walls, ventricular walls etc., in contrast to e.g. blood. Also, electrical signals will typically be voltage or current signals, but may be specifically for determining impedance, capacitance, reactance etc. Further, the signal measured by any one electrode segment may be with reference to a common ground potential (unipolar), an individual ground potential, or to that of another electrode segment (bipolar).

It is understood by the person skilled in the art that the electrical signal from each electrode segment is typically a function of time, and that comparison are performed based on corresponding times for each electrode segment.

Which electrode segments that touch tissue may be determined by determining the impedance between electrode pairs of electrode segments from different bands and arranged on the same side of the catheter. Such impedance measurement is preferably carried out using a four-wire approach to eliminate or reduce the impedance contribution from the wires. The reason being that for MRI adapted EP catheters, so called MR-EP catheters, these wires are highly resistive.

Therefore, in a preferred embodiment, the workstation further comprises a four wire impedance measuring setup for measuring an impedance between first and second electrode segments, and the comparison of the processing unit comprises calculating an impedance between the first and second electrode segments from the detected electrical signals from the first and second electrode segments.

The above embodiment applies the electrical impedance (ratio of voltage to current) to characterise tissue. The person skilled in the art will recognise that the admittance (ratio of current to voltage) may be applied equivalently. In some relations, it is customary to use the term immittance when referring to either the impedance or the admittance of an electrical circuit.

In a second aspect, the invention provides a computer program product for identifying electrode segments that are in contact with tissue, the product comprising software applications which provides the following when executed by a processor in a workstation of an electrophysiology catheter system comprising an electrophysiology catheter with an elongated distal end portion having a centre axis and being bendable in at least one direction transverse to the centre axis and comprising a plurality of electrically isolated electrode segments for detecting electrical signals and being arranged in two or more longitudinally spaced bands around said end portion:
  identifying electrode segments that are in contact with tissue from the received electrical signals by comparing electrical signal from each electrode segment with that from one or more other electrode segments or a predetermined threshold value; and
  presenting the identified electrode segments to an operator with an indication of the identified electrode segments' position in relation to a bending direction or another marker of roll angle of the distal end portion.

In a third aspect, the invention provides a computer program product for updating a workstation in an electrophysiology catheter system to identify electrode segments that are in contact with tissue, the product comprising means for installing software applications which provides the following when executed by a processor in a processing unit of an electrophysiology catheter system comprising an electrophysiology catheter with an elongated distal end portion having a centre axis and being bendable in at least one direction transverse to the centre axis and comprising a plurality of electrically isolated electrode segments for detecting electrical signals and being arranged in two or more longitudinally spaced bands around said end portion:
  identifying electrode segments that are in contact with tissue from the received electrical signals by comparing electrical signal from each electrode segment with that from one or more other electrode segments or a predetermined threshold value; and
  presenting the identified electrode segments to an operator with an indication of the identified electrode segments' position in relation to a bending direction or another marker of roll angle of the distal end portion.

The second and third aspect of the invention relates to computer program products. Such computer program product is adapted to enable a computer system comprising at least one computer having data storage means associated therewith to control an EP catheter system or a processing unit of such to carry out the invention. These aspects of the invention are particularly, but not exclusively, advantageous in that the present invention may be implemented by a computer program product enabling a computer system to perform the operations of the first aspect of the invention. Thus, it is contemplated that some known EP catheter system, or a processing unit of such, may be changed to operate according to the present invention by installing a computer program product on a computer system controlling the EP catheter system. Such a computer program product may be provided on any kind of computer readable medium, e.g. magnetically or optically based medium, or through a computer based network, e.g. the Internet.

In a fourth aspect, the invention provides a method for analysing electric signals from an electrophysiological catheter with an elongated distal end portion having a centre axis and being bendable in at least one direction transverse to the centre axis and comprising a plurality of electrically isolated electrode segments for detecting electrical signals and being arranged in two or more longitudinally spaced bands around said end portion to obtain information of which, if any, electrode segments in contact with tissue, the method comprising:
  comparing electrical signal from each electrode segment with that from one or more other electrode segments or a predetermined threshold value; and
  as an outcome of the comparison, identifying electrode segments that are in contact with tissue;
  presenting the identified electrode segments to an operator with an indication of the identified electrode segments' position in relation to a bending direction or another marker of roll angle of the distal end portion.

The method according to the fourth aspect thereby corresponds to the functionality in the system of the first aspect, and the first through fourth aspects all aim at obtaining the first object of the invention.

The second object of the present invention is to provide a system, a computer program and a method that solves the problems of the prior art with filtering gradient induced artefacts on EP signals measured with MR-EP catheters.

The above described first object is intended to be obtained, in a fifth aspect of the invention, by providing an electrophysiology catheter system for use in combination with a MRI apparatus, electrophysiology catheter system comprising:
an MR-EP catheter with an elongated distal end portion, comprising:
  a plurality of electrically isolated electrode segments for detecting electrical signals and being arranged in two or more longitudinally spaced bands around said end portion;
  a plurality of electrode wires each coupled to an electrode segment and extending through the distal end portion to a proximal end portion of the electrophysiology catheter; and
  a workstation arranged to receive electrical signals detected by each electrode segment by means of the electrode wires coupled thereto and comprising a processing unit configured to determine a reference signal for gradient induced artefacts on an electrophysiological signal of an electrode segment from electrical potential differences between electrode segments.

The invention is particularly, but not exclusively, advantageous for obtaining a reference signal which allows artefacts induced by the gradient field of an MRI apparatus to be efficiently and easily removed. This makes it simpler to filter EP signals and thereby decreases cost and complexity of MR-EP catheter systems.

Therefore, in a preferred embodiment, the processing unit is further configured to correct the electrophysiological signal from an electrode by adaptive filtering using said reference signal.

In a sixth aspect, the invention provides a computer program product for determining a reference signal for gradient induced artefacts, the product comprising software applications which provides the following when executed by a processor in a processing unit of an electrophysiology catheter system comprising a MR-EP catheter with an elongated distal end portion and comprising a plurality of electrically isolated electrode segments for detecting electrical signals and being arranged in two or more longitudinally spaced bands around said end portion:
    determine a reference signal for gradient induced artefacts on an electrophysiological signal of an electrode segment from electrical potential differences between electrode segments.

In a seventh aspect, the invention provides a computer program product for updating a workstation in an electrophysiology catheter system to determine a reference signal for gradient induced artefacts, the product comprising means for installing software applications which provides the following when executed by a processor in a processing unit of an electrophysiology catheter system comprising an MR-EP catheter with an elongated distal end portion and comprising a plurality of electrically isolated electrode segments for detecting electrical signals and being arranged in two or more longitudinally spaced bands around said end portion:
    determine a reference signal for gradient induced artefacts on an electrophysiological signal of an electrode segment from electrical potential differences between electrode segments.

The sixth and seventh aspect of the invention relates to computer program products. Such computer program product is adapted to enable a computer system comprising at least one computer having data storage means associated therewith to control an EP catheter system or a processing unit of such to carry out the invention. These aspects of the invention are particularly, but not exclusively, advantageous in that the present invention may be implemented by a computer program product enabling a computer system to perform the operations of the fifth aspect of the invention. Thus, it is contemplated that some known EP catheter system, or a processing unit of such, may be changed to operate according to the present invention by installing a computer program product on a computer system controlling the EP catheter system. Such a computer program product may be provided on any kind of computer readable medium, e.g. magnetically or optically based medium, or through a computer based network, e.g. the Internet.

In an eighth aspect, the invention provides a method for analysing electric signals from a MR-EP catheter with an elongated distal end portion and comprising a plurality of electrically isolated electrode segments for detecting electrical signals and being arranged in two or more longitudinally spaced bands around said end portion to determine a reference signal for gradient induced artefacts, the method comprising determining a reference signal for gradient induced artefacts on an electrophysiological signal of an electrode segment from electrical potential differences between electrode segments.

The method according to the eighth aspect thereby corresponds to the functionality in the system of the fifth aspect, and the fifth through eighth aspects all aim at obtaining the second object of the invention.

The basic idea for obtaining the first object of the invention is that since the electrical signal detected by an electrode segment to a relatively large degree depends of whether the electrode segment touches connected tissue or only blood, these signals and knowledge of each segment's position can be used to determine roll angle information of the catheter in relation to patient anatomy.

The basic idea for obtaining the second object of the invention is that adjacent electrode segments forming a band around the MR-EP catheter compare to a closed loop. Therefore, the summed electrical potential of these segments will equal zero in the absence of a gradient field, and the discrepancy from this condition in the presence of a gradient field can be used to extract a reference signal that can be used to correct for gradient induced artefacts.

The individual aspects of the present invention may each be combined with any of the other aspects. These and other aspects of the invention will be apparent from the following description with reference to the described embodiments.

BRIEF DESCRIPTION OF THE FIGURES

Various embodiments according to the invention will now be described in more detail with regard to the accompanying figures. The figures show one way of implementing the present invention and is not to be construed as being limiting to other possible embodiments falling within the scope of the attached claim set.

DETAILED DESCRIPTION OF AN EMBODIMENT

The basic hardware for use in various embodiments of the invention will be described in the following in relation to FIGS. 1 through 3.

Figure 1:
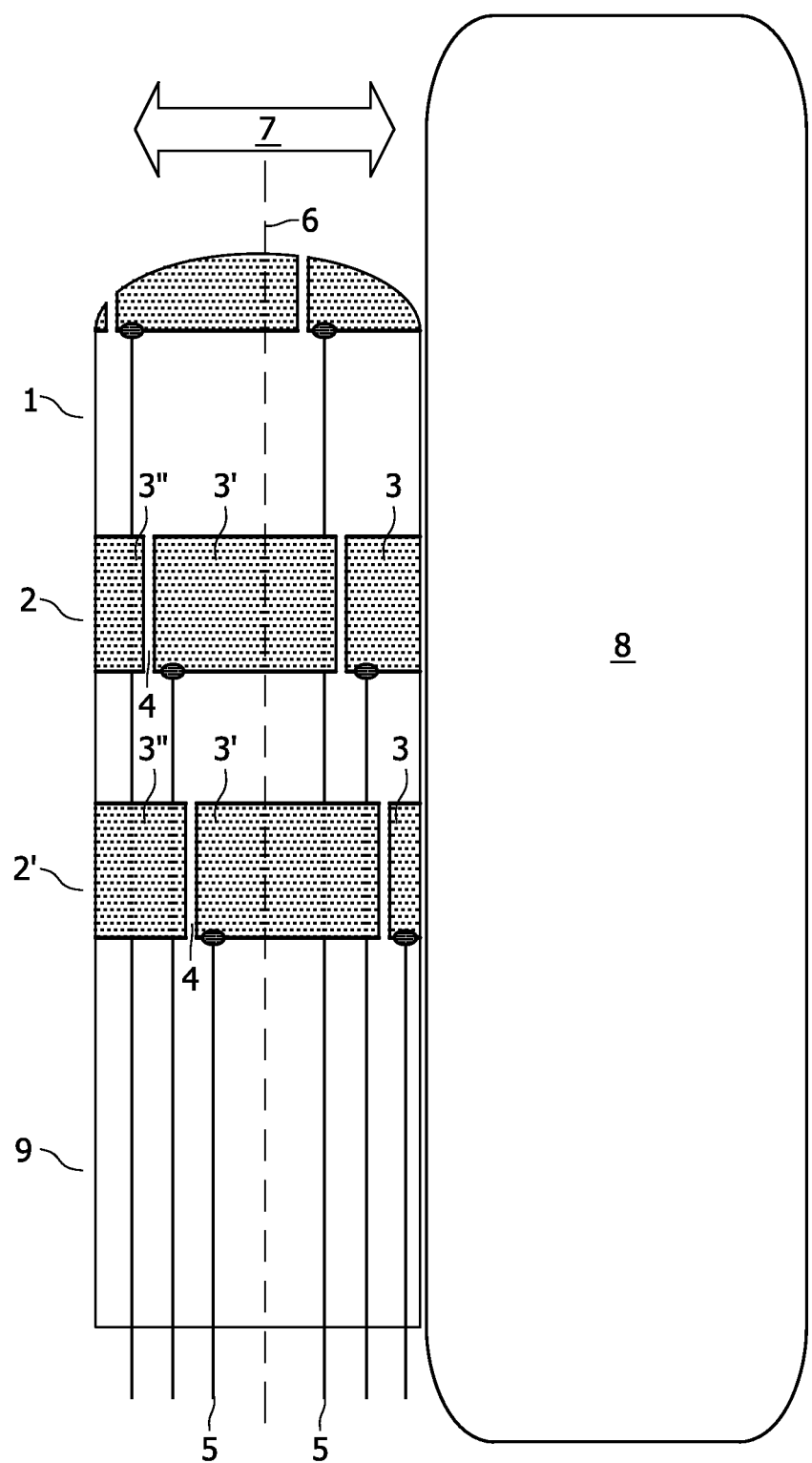
FIGS. 1 and 2 are illustrations of a distal end portion of an EP catheter forming part of various embodiments according to the invention.
Figure 2:
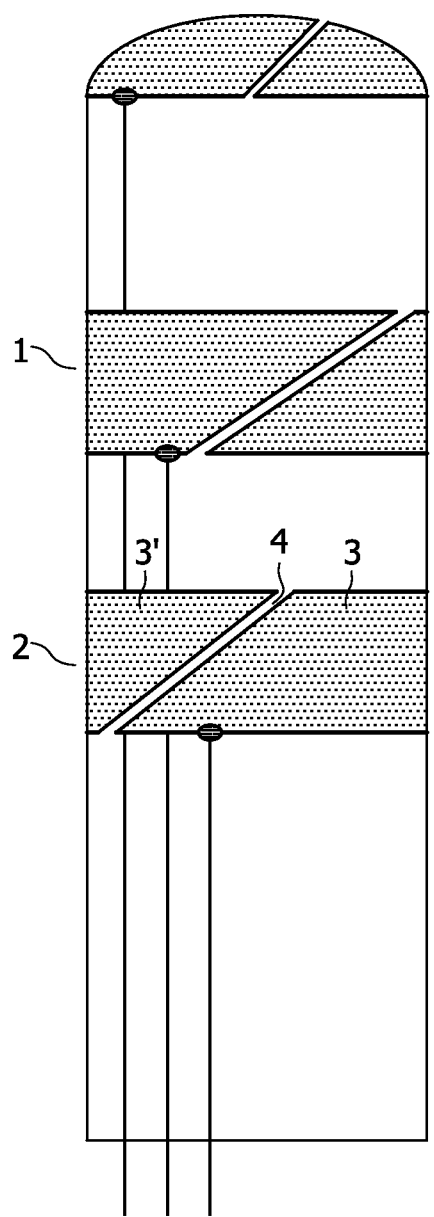

FIG. 1 shows a distal end portion 1 of an EP catheter 9 according to various embodiments of the invention. A centre axis for the distal end portion is illustrated by punctured line 6. Distal end portions of catheters are normally bendable to facilitate steering of the catheter during advancement in a patient. Arrow 7 illustrates a bending direction of the distal end portion 1 being transverse to the centre axis 6.

Electrode segments 3 (3', 3") are arranged in bands 2 around the end portion to detect and thereby map electrophysiological signals in patient anatomy. It is customary to have many bands, such as around 20 bands, around such EP catheter. The electrode segments are separated by slits 4 to electrically isolate them from each other.

It is preferred that such slits 4 are narrow to avoid dead regions with no electrode coverage around the catheter. For that reason, it may also be preferred to arrange slits 4 diagonally, i.e. non-parallel to the centre axis 6, as shown in FIG. 2.

Figure 3:
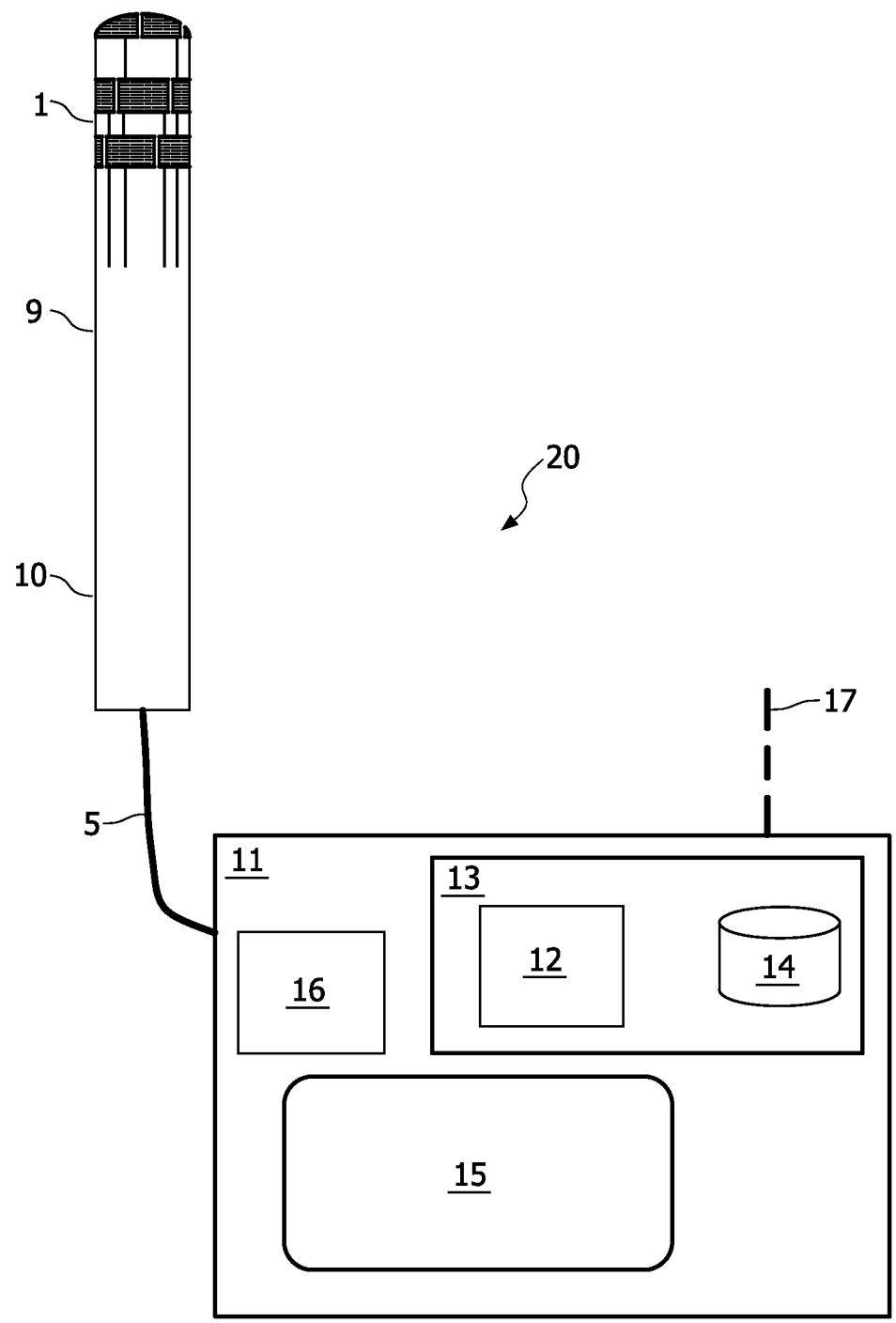
FIG. 3 is an illustration of an embodiment of an EP catheter system according to the invention.

Each electrode segment 3 is coupled to an electrode wire 5 extending, now turning to FIG. 3, through the distal end portion 1 to a proximal end portion 10 and to a workstation 11 of a electrophysiology catheter system 20.

FIG. 3 illustrates an embodiment of an EP catheter system 20, comprising the EP catheter 9 and the workstation 11 as the main components. The work station 11 may be a dedicated EP workstation, an MRI workstation, other medical imaging workstations, or combined workstation of any of these. The workstation serves the function of collecting equipment such as cables, processing units, displays, user interfaces for the various appliances as well as power supplies and connections for such equipment in a practical, robust and transportable casing. Typically, the workstation also hosts means, different from wires 5, to receive data and software, such as a network connection 17, a CD ROM drive (not shown) or similar.

In a preferred embodiment, a processing unit 13 of the workstation equals a computer with processor 12 and memory 14 for holding computer programs, i.e. software, to be executed by the processor. The workstation 11 can typically present measured and/or analysed date to an operator in a graphical user interface on a display 15.

Also, the workstation can contain dedicated circuitry 16 related to the measurement of electrical signals from electrode segments comprising components such as amplifiers, samplers, multipliers, filters, current supply etc.

In the following, embodiments related to the different aspects of the invention related to determining information related to a roll angle will be described.

In a preferred embodiment, the processing unit 13 is configured to identify electrode segments 3 that are in contact with wall 8 consisting of connected tissue as shown in FIG. 1. This can be realised by comparing the electrical signal from each electrode segment with that from one or more other electrode segments or a predetermined threshold value.

In the situation shown in FIG. 1 electrodes 3 from bands 2 and 2' touch tissue 8 whereas electrodes 3' and 3" from bands 2 and 2' will be floating in blood. The electrograms (the electrical signal from electrode segments as a function of time) differ if they stem from an electrode segment touching the cardiac wall ("wall signal" from electrodes 3) or an electrode segment floating in blood ("blood signals" from electrodes 3' and 3"), and these can be distinguished by visual inspection by an experienced electrophysiologist.

The comparison of the electrical signals from electrode segments to determine which are "wall signals" and which are "blood signals" can be carried out by several different scenarios, such as the following, alone or in combination:

Comparing magnitudes of electrical signals from different electrode segments within a band.

Comparing magnitudes of electrical signals from electrode segments in different bands, such as electrode segments positioned on the same side of the distal portion in different bands.

Comparing a magnitude of the electrical signal from each electrode segments to a predetermined threshold value.

Alternatively, the impedance between each pair of electrodes (3-3, 3'-3', 3"-3") can be measured to determine if a side touches the wall. The resistance between electrodes that float in blood will be smaller that the resistance between those, which touch the wall. Another scenario for comparing electrode signals is thereby to compare magnitudes of electrical signals from a pair of electrode segments to determine modalities such as impedance between such electrode segment pair, and comparing the impedance to impedances between different pairs or to a threshold value.

Especially for MR-EP catheters where the wires 5 are highly resistive, it is preferred to use a four wire impedance measuring setup. Such typically comprises an alternating current source connected to provide a current driving signal between a first and a second electrode segment by means of the electrode wires coupled thereto and an impedance measuring circuit for detecting electrical voltage signal between said first and second electrode segment, which employs an additional set of wires coupled to the electrodes.

As a consequence it can be determined with which side the catheter 9 touches the wall 8, and this information can be presented to an operator with an indication of the identified electrode segments' position in relation to a bending direction or other markers for roll angle.

This is important since the distal portion may only be bent in one or two directions. In the situation in FIG. 1, the catheter can be bent in the directions towards and away from the wall 8 as shown by arrow 7. As the "wall signal" will be detected from electrodes 3, this tells the operator that bending the tip in their direction (i.e. to the right in FIG. 1) would steer the catheter into the wall 8, and that the roll angle of the catheter would have to be changed to steer the catheter in directions orthogonal to the wall. Bending the catheter in the right directions can be extremely helpful for guidance at difficult morphologies, e.g. ridge between PV ostiae and appendage.

Figure 4:
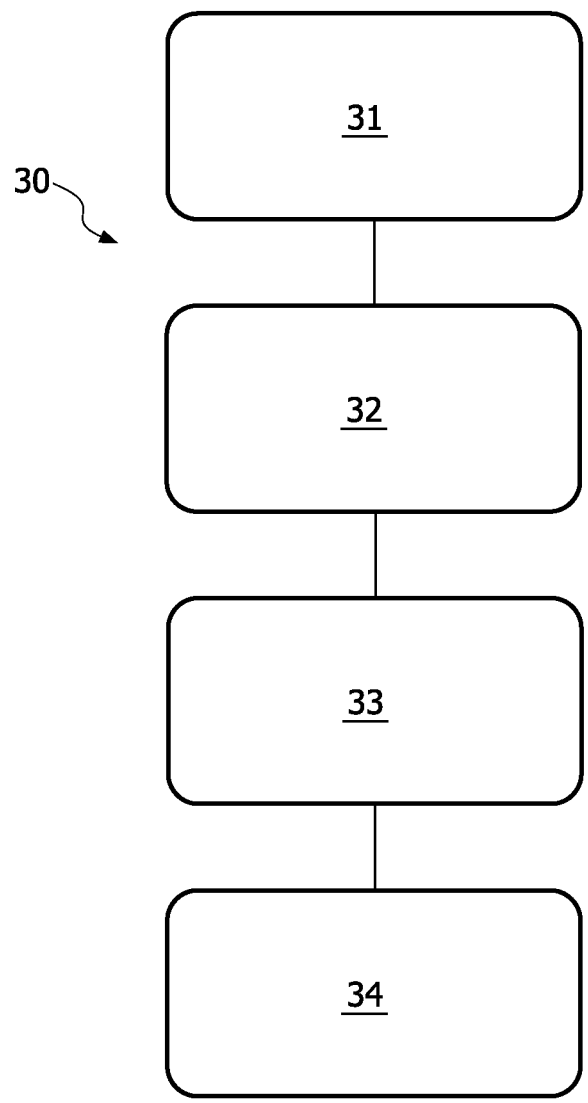
FIG. 4 is a flow-chart describing a method according to embodiments of the invention as well as a schematic system-chart representing an out-line of the operations of a computer program product according to embodiment of the invention.

As described previously, the various aspects can be implemented by means of computer programs running on the processors 12 of the processing unit 13, or programs updating the workstation 11 to run such programs. FIG. 4 represents a flow chart 30 for illustrating a possible architecture of an embodiment of such software products. In addition, the flow chart 30 illustrates an embodiment of the method for analysing electric signals portion to obtain information of electrode segments in contact with tissue in accordance with another aspect of the invention.

In Box 31, electric signals detected by electrode segments are received. Optionally, the signals have undergone preprocessing by dedicated circuitry 16 as mentioned previously. In Box 32, the received electric signals are compared, i.e. using one of the scenarios described previously, to determine which (if any) are "wall signals" and which are "blood signals". In Box 33, electrode segments (if any) that are in contact with connected tissue are identified by determining from which electrode segments the identified "wall signals" originate. In Box 34, the identified electrode segments are presented to an operator with an indication of their position in relation to a bending direction or another marker of roll angle.

In the following, embodiments related to the different aspects of the invention related to determining a reference signal will be described.

EP catheters to be used in MRI environments are adapted to such to ensure that they to not cause (too many or too large) artefacts on the MR images. On the other hand, switched gradient fields from the MRI apparatus induce artefacts on the measured EP signals, which contain similar frequencies as the physiological EP signal and are therefore difficult to distinguish and/or remove. Thus, the measured electrical signal can be expressed as $U_{measured} = U_{EP} + U_{artefact}$, where $U_{artefact}$ is unknown. In order to filter these artefacts it is useful to determine a "reference signal" similar to the $U_{artefact}$ so the EP signal can be determined by subtracting the reference signal from the measured signal. In a preferred embodiment, the processing unit 13 is configured to determine a reference signal for such gradient induced artefacts on the electrophysiological signals measured by the EP catheter.

Figure 5:
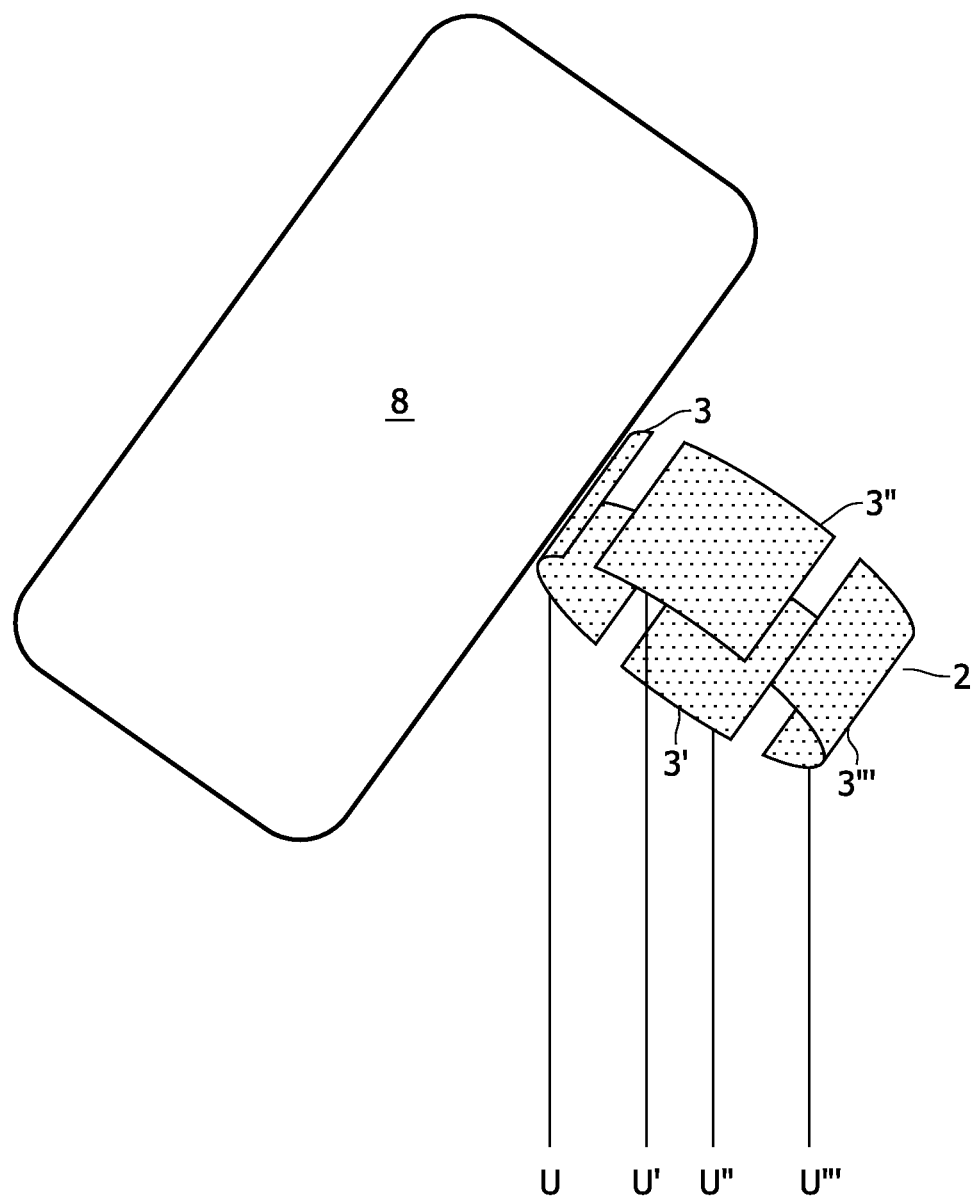
FIG. 5 is an illustration of a measuring setup in accordance with an embodiment of the invention.

As Illustrated in FIG. 5, electrode segments 3, 3', 3'', 3''' arranged in a band 2 each pick up an electrical signal characteristic of the electromagnetic conditions at its position. It can be assumed that the sum of the electrical potentials of all electrode segments in a band equals zero when no gradient field is present. Any remaining signal can thereby be identified as an artefact and a reference signal for the artefact can be determined.

In a specific example of FIG. 5, four different voltages can be measured:

$$V_I = U - U'$$

$$V_{II} = U' - U''$$

$$V_{III} = U'' - U'''$$

$$V_{IV} = U''' - U$$

Furthermore, $V_I + V_{II} + V_{III} + V_{IV} = 0$ must hold, and if the measured sum of these voltages does not equal zero, this is an indication of an artefact. Thus this sum can be used as a reference signal for artefacts, or the deviation from 0 can itself be used as the reference signal.

The determined reference signal can be used to correct for the artefact, e.g. applying an adaptive filter. But also other very simple subtraction filtering approaches can be used to improve the EP signal quality.

Optionally, if the EP signals picked up by segments 3', 3'' and 3''' are significantly reduced because these do not touch the wall, the voltages $V_{II}$ or $V_{III}$ are already good reference signals for gradient induced artefacts. The same holds for bipolar signals measured between electrodes in different rings (2, 2') on the side of the catheter, which does not touch the tissue.

As described previously, the various aspects can be implemented by means of computer programs running on the processors 12 of the processing unit 13, or programs updating the workstation 11 to run such programs. FIG. 4 also represents a flow chart 30 for illustrating a possible architecture of an embodiment of such software products. In addition, the flow chart 30 illustrates an embodiment of the method for determining a reference signal in accordance with another aspect of the invention.

In Box 31, electric signals detected by electrode segments are received. Optionally, the signals have undergone pre-processing by dedicated circuitry 16 as mentioned previously. In Box 32, the electrical potential differences between electrode segments within a band are calculated. In Box 33, a reference signal is determined. In the further optional step of Box 34, an electrophysiological signal from an electrode in the band, preferably one in contact with tissue, is corrected using the determined reference signal, e.g. by adaptive filtering.

The individual elements of an embodiment of the invention may be physically, functionally and logically implemented in any suitable way such as in a single unit, in a plurality of units or as part of separate functional units. The invention may be implemented in a single unit, or be both physically and functionally distributed between different units and processors.

Although the present invention has been described in connection with the specified embodiments, it should not be construed as being in any way limited to the presented examples. The scope of the present invention is to be interpreted in the light of the accompanying claim set. In the context of the claims, the terms "comprising" or "comprises" do not exclude other possible elements or steps. Also, the mentioning of references such as "a" or "an" etc. should not be construed as excluding a plurality. The use of reference signs in the claims with respect to elements indicated in the figures shall also not be construed as limiting the scope of the invention. Furthermore, individual features mentioned in different claims, may possibly be advantageously combined, and the mentioning of these features in different claims does not exclude that a combination of features is not possible and advantageous.

The invention claimed is:

1. An electrophysiology catheter system comprising:
   an electrophysiology catheter with an elongated distal end portion having a centre axis and being bendable in at least one direction transverse to the centre axis, comprising:
   two or more longitudinally spaced bands around said end portion, each band comprising a plurality of electrically isolated electrode segments for detecting electrical signals and being arranged in a band around said end portion;
   a plurality of electrode wires each coupled to an electrode segment and extending through the distal end portion to a proximal end portion of the electrophysiology catheter; and
   a workstation arranged to receive electrical signals detected by each electrode segment by means of the electrode wires coupled thereto and comprising a processing unit configured to identify electrode segments that are in contact with tissue from the received electrical signals by comparison of the electrical signal from each electrode segment with that from one or more other electrode segments or a predetermined threshold value and presenting the identified electrode segments to an operator with an indication of the identified electrode segments' position in relation to a bending direction or another marker of roll angle of the distal end portion.

2. The electrophysiology catheter system according to claim 1, wherein the workstation further comprises a four wire impedance measuring setup for measuring an impedance between first and second electrode segments, wherein the comparison of the processing unit comprises calculating an impedance between the first and second electrode segments from the detected electrical signals from the first and second electrode segments.

3. The electrophysiology catheter system according to claim 1, wherein the workstation comprises a graphical user interface for presenting the positions of electrode segments identified to be in contact with tissue in relation to a bending direction or another marker of roll angle of the distal end portion.

4. A computer program product embodying computer instructions on a non-transitory computer readable medium, for identifying electrode segments that are in contact with tissue, the product comprising software applications which provides the following when executed by a processor in a processing unit of an electrophysiology catheter system comprising an electrophysiology catheter with an elongated distal end portion having a centre axis and being bendable in at least one direction transverse to the centre axis and comprising a plurality of electrically isolated electrode segments for detecting electrical signals and being arranged in two or more longitudinally spaced bands around said end portion:
- identifying electrode segments that are in contact with tissue from the received electrical signals by comparing electrical signal from each electrode segment with that from one or more other electrode segments or a predetermined threshold value; and
- presenting the identified electrode segments to an operator with an indication of the identified electrode segments' position in relation to a bending direction or another marker of roll angle of the distal end portion.

5. A method for analysing electric signals from an electrophysiological catheter with an elongated distal end portion having a centre axis and being bendable in at least one direction transverse to the centre axis and comprising a plurality of electrically isolated electrode segments for detecting electrical signals and being arranged in two or more longitudinally spaced bands around said end portion to obtain information of which, if any, electrode segments in contact with tissue, the method comprising: comparing electrical signal from each electrode segment with that from one or more other electrode segments or a predetermined threshold value; and as an outcome of the comparison, identifying electrode segments that are in contact with tissue; presenting the identified electrode segments to an operator with an indication of the identified electrode segments' position in relation to a bending direction or another marker of roll angle of the distal end portion.

* * * * *